(12) United States Patent
Moles et al.

(10) Patent No.: US 6,551,496 B1
(45) Date of Patent: Apr. 22, 2003

(54) MICROSTRUCTURED BILATERAL SENSOR

(75) Inventors: Donald R. Moles, Cedarville, OH (US); Quinn Leland, Kettering, OH (US); Marcel Madaras, Rochester, NY (US)

(73) Assignee: YSI Incorporated, Yellow Springs, OH (US)

( * ) Notice: Subject to any disclaimer, the term of this patent is extended or adjusted under 35 U.S.C. 154(b) by 125 days.

(21) Appl. No.: 09/800,438

(22) Filed: Mar. 6, 2001

Related U.S. Application Data

(60) Provisional application No. 60/186,930, filed on Mar. 3, 2000.

(51) Int. Cl.[7] .................................................. G01N 27/327
(52) U.S. Cl. ............... 205/778; 204/403.1; 204/403.11
(58) Field of Search ..................... 204/403.01, 403.06, 204/403.1, 403.11, 409; 205/778, 777.5

(56) References Cited

U.S. PATENT DOCUMENTS

| | | |
|---|---|---|
| 2,510,262 A | 6/1950 | Sollner et al. |
| 3,539,455 A | 11/1970 | Leland, Jr. |
| 3,668,101 A | 6/1972 | Bergman |
| 4,073,713 A | 2/1978 | Newman |
| 4,454,007 A | 6/1984 | Pace |
| 4,680,268 A | 7/1987 | Clark, Jr. |
| 4,721,677 A | 1/1988 | Clark, Jr. |
| 4,858,883 A | 8/1989 | Webster |
| 4,874,500 A | 10/1989 | Madou et al. |
| 4,889,611 A | 12/1989 | Blough, Jr. |
| 5,063,081 A | 11/1991 | Cozzette et al. |
| 5,120,504 A | 6/1992 | Petro-Roy et al. |
| 5,194,133 A | 3/1993 | Clark et al. |
| 5,238,548 A | 8/1993 | van der Wal et al. |
| 5,350,518 A | 9/1994 | Hiti et al. |
| 5,393,401 A | 2/1995 | Knoll |
| 5,443,890 A | 8/1995 | Ohman |
| 5,468,374 A | 11/1995 | Knoll |
| 5,660,728 A | 8/1997 | Saaski et al. |
| 5,846,392 A | 12/1998 | Knoll |
| 5,882,494 A | 3/1999 | Van Antwerp |
| 5,932,799 A | 8/1999 | Moles |
| 6,073,482 A | 6/2000 | Moles |

FOREIGN PATENT DOCUMENTS

| | | |
|---|---|---|
| EP | 0 750 744 B1 | 10/1995 |
| WO | WO 95/08716 | 3/1995 |

OTHER PUBLICATIONS

S. Sampath and O. Lev, "Inert Metal–Modified, Composite Ceramic–Carbon, Amperometric Biosensors: Renewable, Controlled Reactive Layer", 7/96, *Analytical Chemistry*, vol. 68, No. 13.

J. Perdomo et al., "Containment sensors for the determination of L–lactate and glucose", 8/98, *Biosensors & Bioelectronics*.

D. Thevenot, "Problems in Adapting a Glucose–Oxidase Electrochemical Sensor into an Implantable Glucose–Sensing Device", May–Jun. 1982, *Diabetes Care*, vol. 5 No. 3.

R. Steinkuhl et al., "Glucose Sensor in Containment Technology", 1994, *Horm. Metab. Res. 26*.

Primary Examiner—Jill Warden
Assistant Examiner—Alex Noguerola
(74) Attorney, Agent, or Firm—Thompson Hine LLP

(57) ABSTRACT

A bilateral biosensor based upon a microporous architecture is provided which seeks to reduce the effect of co-reactant concentration limitations by utilizing a new sensor microgeometry. If implemented on the appropriate scale, the new sensor design augments substantially the concentration of oxygen, or other co-reactants or reagents, in the reaction zone of the sensor. Performance enhancements over traditional microscale devices employing unilateral orientation are accomplished, in one embodiment, by allowing analyte to enter the sensor from one side of the sensor, while allowing a co-substrate to enter from both sides of the sensor.

28 Claims, 3 Drawing Sheets

MICROSTRUCTURED BILATERAL SENSOR

This application claims the benefit of provisional application Ser. No. 60/186,930 filed Mar. 3, 2000.

BACKGROUND

The invention relates to sensors and more particularly biosensors based upon a microporous architecture.

One of the earliest patents describing biosensors is U.S. Pat. No. 3,539,455 to Clark, in which a membrane-covered polarographic probe transduces hydrogen peroxide created by entrapped glucose oxidase enzyme. In the thirty years since that patent issued, many other patents have focused upon the layering of materials and reagents to yield better performing sensors. Many of these patents have in common a method of biosensor construction which generally consists of a membrane composed of various functional layers, including an immobilized enzyme layer, all superimposed upon an electrode, or set of electrodes. In this configuration the analytes, chemical co-factors or other influences all approach the electrochemical transducer from one side, the face, or front of the sensor. In its most common manifestation, the face of the electrode probe, covered by the membrane, is situated in a buffer-filled sample chamber into which a sample is injected. Some of the substrate diffuses through the membrane. Using a glucose sensor as an example, when the glucose contacts the immobilized oxidase enzyme, it is rapidly oxidized, producing hydrogen peroxide. Oxygen is necessary for the reaction to proceed; this substrate also must enter the sensor from the front. The oxidase enzyme catalyzes the reaction of glucose and oxygen to produce Glucono-δ-lactone and hydrogen peroxide. The peroxide is, in turn, oxidized at the platinum anode, producing electrons. A dynamic equilibrium is achieved when the rate of $H_2O_2$ production and the rate at which $H_2O_2$ leaves the immobilized enzyme layer are constant and is indicated by a steady state response. The electron flow is linearly proportional to the steady state $H_2O_2$ concentration and, therefore, to the concentration of the analyte, glucose.

In the sensor described above, when the sensor is exposed to high glucose concentrations it is very possible that insufficient oxygen will be present to support the conversion of all of the available glucose in the enzyme layer to the reaction products. For example, if the sensor is implanted, the oxygen levels in the blood are not sufficient to support the glucose reaction. In this case the reaction is considered to be "oxygen limited" and the sensor will not give a linear response to further increases in glucose concentration. Oxygen limitation may be caused by low oxygen concentration in the analyte matrix, e.g., blood, a relatively low diffusivity of oxygen through the materials used in the construction of the sensor and, lastly, relatively long distances (on a molecular scale) which separate the oxygen source and the reaction site. Efforts to circumvent these limitations have focused upon the materials, as well as, the basic sensor chemistry itself. Some of the contemporary development of this type of biosensor has focused upon the selection, or formulation, of materials which limit the diffusion of the analytes (e.g. glucose) more than the secondary substrate, in this case oxygen, so as to reduce non-linearity due to oxygen limitation. This approach is used in U.S. Pat. No. 5,882,494. While extending the typical linear range of the device, this approach also reduces the sensitivity of the device due to the increased diffusional resistance of the outer membrane to the analyte. This tradeoff between sensitivity and linearity has been a major obstacle to the use of these sensors. Sensors with good sensitivity usually exhibit poor linearity and vice-versa. In applications where the sensor is to be employed in-vivo the developer seeks to keep the device as small as possible, so as to minimize it's invasiveness. Smaller dimensions generally tend to restrict electrode area and consequently reduce the available signal. In applications such as these, it is desirable to preserve as much signal as possible, despite the reduced size.

SUMMARY OF INVENTION

One object of the invention seeks to reduce the effect of co-reactant concentration limitations in sensor design by proposing a new sensor microgeometry which, if implemented on the appropriate scale, augments substantially the concentration of oxygen, or other co-reactants or reagents, in the reaction zone of the sensor. This is accomplished in one embodiment by allowing analyte to enter the sensor from one side of the sensor, while allowing a co-substrate to enter from both sides of the sensor. The extreme thinness of the sensor that is feasible can serve to increase the angle of acceptance of the oxygen molecules, but more importantly, it can greatly increase the steepness of the oxygen concentration gradient, which in turn directly affects the rate of oxygen diffusion. The result of this design approach is sensor performance well beyond that obtained from traditional microscale devices employing unilateral orientation. Performance enhancements are especially apparent in the areas of sensitivity, linear range and low-oxygen tolerance.

A microporous biosensor is provided which comprises a substrate having at least one pore therein extending from a front surface of the substrate to the back surface, the pore having an enzyme-containing membrane near the front face of the pore on one surface of the substrate and an electrode in electrochemical conductive contact with the enzyme-containing membrane. The electrode can be deposited on the wall of the pore or adjacent to the perimeter of the pore on the back surface of the substrate. In one embodiment of the invention, a back membrane is provided across the back face of the pore. The back membrane can function as a hydrodynamic stabilizer to prevent fluids from flowing freely through the pore. The back membrane is permeable to a co-substrate, co-reactant or other reagent for the analytical reaction, which occurs as the analyte contacts the enzyme at or near the front face of the pore. In the most typical embodiments of the invention, the biosensor includes a plurality of pores which may be arranged in a random or ordered pattern within the substrate.

The invention is the result of studies directed to improving sensor performance. In one embodiment sensor performance is improved by preferentially supplying a co-substrate for the analytical reaction from the back side of the sensor through the pore. For example, one embodiment of the invention is a glucose sensor in which oxygen is preferentially supplied from the backside of the sensor. The sensor can be implemented in one mode in which the front and back faces of the sensor contact the same medium, e.g., blood, as in the case of an in vivo implanted sensor. The membrane at the front side of sensor is designed to allow an analyte such as glucose to diffuse into the membrane and react with a co-substrate such as oxygen. The back side membrane, however, is different than the front side and is designed to preferentially allow the co-substrate, often in the absence of analyte, to diffuse through the pore. In this way co-substrate supplied through the pore augments co-substrate supplied in the analyte-containing medium at the front face of the pore and overcomes co-substrate concentration limitations on the analysis.

In the second mode in which the sensor can be used, the medium to which the back of the sensor is exposed is different than the medium containing the analyte. The back side medium can be one which is augmented with the co-substrate. Using a microfluidic glucose analyzer as an example, the backside of the sensor can be open to the air, an oxygen gas reservoir or an oxygen-containing liquid so that oxygen preferentially diffuses through the back membrane and through the pore where it augments the oxygen in the blood which contacts the front face of the sensor.

In another manifestation of the invention, instead of preferentially supplying a co-substrate from the back side of the sensor, other reagents can be supplied. For example, in many cases it may be desirable to maintain a predetermined pH at the enzyme membrane. By supplying an acidic, basic, or a buffered solution from the backside, the optimum pH for the enzyme reaction can be assured.

In still another manifestation of the invention a cofactor such as NADH can be provided from the backside of the sensor.

It will also be recognized that the microporous architecture used in the invention provide inherently reduced diffusion times and that this augments the effect of supplying co-substrates and other reagents from the back side of the sensor because these co-reactants can readily and quickly transport from their source at the back of the sensor over the short distances to the enzyme containing membrane where they can react with a satisfactory response time.

The sensors of the invention can be used in microfluidic devices of the type taught in U.S. Pat. Nos. 5,846,392 and 5,932,799 and in sensors of the type described in U.S. Pat. Nos. 3,539,455 and 4,073,713 to Clark and in sensors similar to the YSI 2700 Select from YSI Incorporated of Yellow Springs, Ohio.

DETAILED DESCRIPTION OF THE INVENTION

Figure 1:
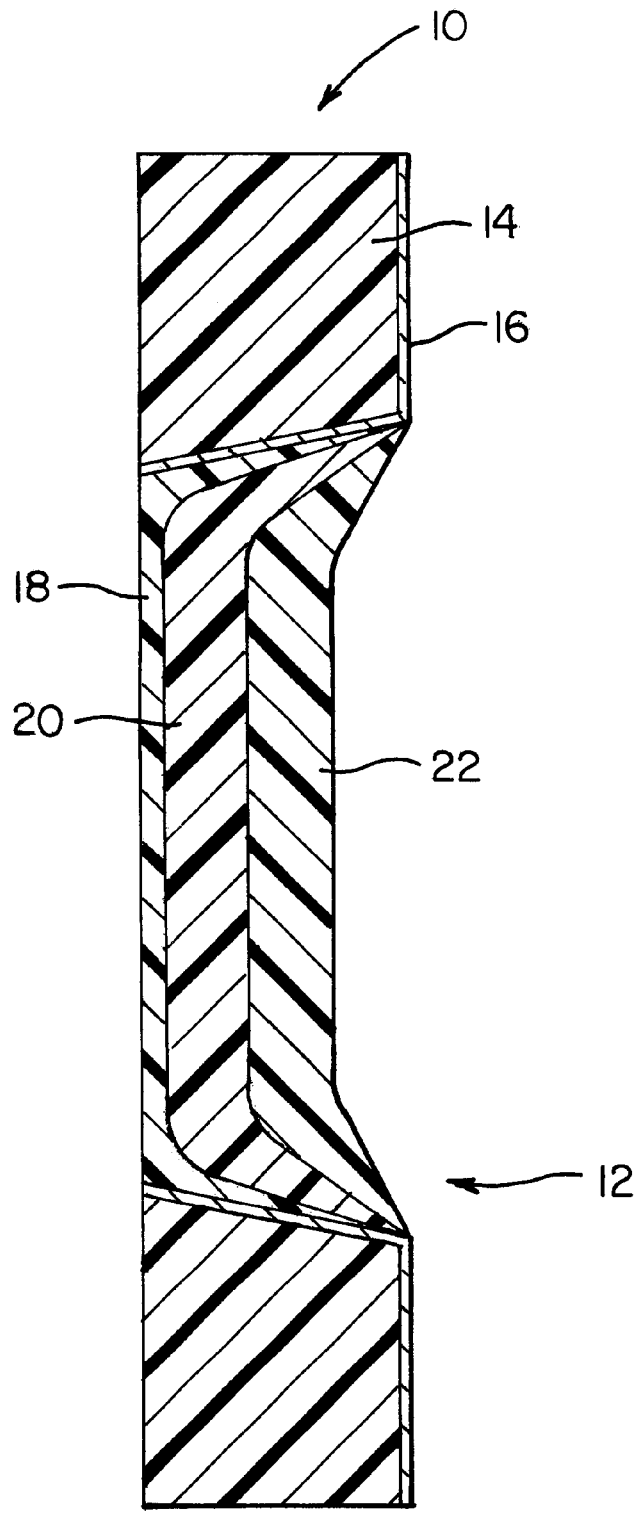
FIG. 1 is a cross-sectional schematic view of a sensor in accordance with one embodiment of the invention.

Any of the enzymes and membranes previously disclosed or hereafter developed for use in enzyme electrodes should be useful in forming the enzyme-containing membrane used in the invention. One such membrane is described in U.S. Pat. No. 4,073,713 to Clark and includes, as the enzyme, glucose oxidase, galactose oxidase or uricase. In addition to these enzymes, other enzymes that can be used in the invention include all the oxidases listed in the Table at columns 9–12 in U.S. Pat. No. 4,721,677 to Clark, 1988.

The enzyme layer is a thin porous matrix that holds the enzyme and permit the analyte to contact the enzyme. The matrix may be formed of materials such as glutaraldehyde, PBS, and other suitable membranes disclosed in U.S. Pat. No. 4,721,677 and in Table I of Thevenot, D. R., Problems in adapting a glucose-oxidase electrochemical sensor into an implantable glucose-sensing device, Diabetes Care, 5(3): 184–198, 1982 in which the entire contents therein is incorporated herein by reference. In one embodiment of the invention the enzyme will range in thickness from about 0.5 $\mu$m to 200 $\mu$m.

In one embodiment of the invention a thin barrier film is provided over the enzyme membrane on the front face of the pore. This barrier film may function to prevent the enzyme from migrating from the membrane into the analyte containing fluid or medium. The barrier film must be permeable to the analyte, and preferably the co-substrate also. The barrier film can be formed from polyvinyl alcohol, polyurethane, polyvinyl chloride, cellulose acetate, polymethacrylates such as polyhydroxyethyl methacrylates, polyhydroxymethyl methacrylates, aerogels, hydrogels, etc. In one embodiment a glucose sensor is provided having a polyvinyl alcohol barrier film. Conventionally, barrier films have been employed in some sensors to restrict the diffusion of analyte to the enzyme membrane. When sensors are constructed using the proposed microstructure the diffusional resistance is less critical because there is back side access to the co-substrate. However, if the sensor is required to operate at extremely low levels of oxygen concentration, employing a barrier film increases the sensor's linearity by limiting the rate of analyte diffusion through the front of the sensor, thereby reducing the equilibrium levels of oxygen needed by the enzymatic reaction. The selection of the barrier film will depend on the application of the sensor, the characteristics of the analyte and the enzyme membrane. An important objective of the barrier is to prevent enzyme migration and thereby maintain the reproducibility or the consistency of the sensor. However, the barrier also increases the sensitivity of the sensor by reducing diffusion of $H_2O_2$ from the pore back into the analyte solution. The barrier film also reduces the influence of flow rate on sensor stability.

In one embodiment, the barrier film can be about 0.5 $\mu$m to 50 $\mu$m thick. The barrier film is typically prepared by preparing a solution of the polymer and drawing down the solution on the back surface of the pore-containing substrate before putting in any enzyme. The concentration and composition of the solution is adjusted so that the surface energy or capillary force draws the solution into the pores and surface tension allows for the formation of a film across the pore. It is particularly effective to use solutions of polar solvents with a hydrophilic pore.

The substrate can be substantially any planar substrate that has the requisite mechanical properties to form at least one pore therein and to support the electrode and the films which are described herein. Representative examples of useful films are polyimide (Kapton™, Upilex™), polycarbonate (PC), polyester (Mylar™), polyethylene terephthalate (PET). polyethylene naphthalate (PEN, Kaladex™). Silicon or ceramic substrates may also be useful. To maintain reasonable response times and to use materials that are readily available, in one embodiment the films used as substrates in the invention usually will lie in a range of about 1 to 1000 micron thick and are still more usually in a range of about 1 to 200 micron. In another embodiment the substrate is about 5 to 100 micron thick.

In most cases the acceptable response time of a sensor is in the range of seconds, to tens of seconds. Response time is partially a function of sensor dimensions by way of the phenomenon of diffusion, the thermally driven movement of molecules across a concentration gradient. The sensor is preferably scaled appropriately to the distance that analyte molecules will move, via diffusion, over the time course of the measurement to provide minimal or an acceptable response. This distance usually ranges from microns to a few hundred microns. An electrode can be fashioned so as to permit the diffusion of analyte to its surface from both its front side and its back side if the electrode is made from a thin porous, preferably micro-porous, film. The overall objective in the design of the electrode is to create a catalytically active surface, which remains intimate with the source(s) of the reaction substrates without significantly obstructing their free movement. The porous sensor described herein satisfies this requirement very well if the pores are relatively small when compared to average diffusion distances.

The pore(s) can be formed in the film by any of a variety of processes including microetching, micromachining, embossing and micromolding. A particularly useful process is laser drilling. Holes are drilled through the target material by UV photochemical ablation, utilizing an excimer laser source operating at a suitable emission wavelength (typically 193, 248, 308 or 355 nm). The output beam of the laser is directed through a suitable mask (typically a metal stencil or a patterned film coating on a transparent substrate) consisting of one or more apertures defining the hole or hole pattern to be drilled. The portion of the beam transmitted through the mask is imaged upon, and appropriately aligned to the target material, at an optical demagnification ratio sufficient to achieve suitable energy density on the target material to effect the desired photochemical ablation process. A sufficient number of laser pulses at this energy density is then applied to the target material to carry the photochemical ablation process through the full thickness of the target material. The projected mask image is then repositioned with respect to the target material to drill additional holes or hole patterns in a similar fashion. A single beam laser can also be used to form the pores.

The pores can range in diameter from about 2 to 200 microns and more preferable from about 1 to 100 microns. Pores formed by these methods will generally have a frustoconical shape being smaller in diameter at the front face of the sensor than at the back. This frustoconical shape provides a surface upon which an electrode can be deposited on the inside of the pore. The number of pores used in the sensor can be adjusted so as to provide the desired current for the concentrations of analyte that are measured. If the pores are spaced so that they are not competing with one another for analyte, the current will be proportional to the total surface are of the pores.

In another embodiment of the invention cyclotron irradiated films can be used. The pores in these films will be randomly distributed and can range in pore size from about 0.02 to 2 microns. Between this process and the other processes mentioned herein, the pores range from about 0.02 to 200 microns in diameter in one embodiment. The pore geometry, e.g., depth and radius, can be optimized based on the relative diffusion characteristics of the analyte and the reaction products through the pore membranes so as to provide the desired response times. For example for measuring glucose in a pore sensor employing a PVA membrane to provide response times less than 180 seconds, in one embodiment pore depth (substrate thickness) should be less than 85 microns and most preferably less than 50 microns and the pore diameter should be less than 80 microns and preferably less than 50 microns.

In accordance with the invention, the back side of the sensor is opened up to co-reactants or reagents for the analytical reaction, e.g. oxygen in the case of a glucose sensor based on an oxidase enzyme. This increases greatly the equilibrium concentrations of the co-substrate or co-reactant molecules, reducing or effectively eliminating the chance that they will become limiting. The increased co-substrate concentration allows for a concomitant increase in absolute analyte concentration that can be linearly reacted, which, in turn, allows for less restrictive diffusion control of the analyte molecules. The increased equilibrium concentration of analyte inside the immobilized enzyme matrix translates into higher hydrogen peroxide generation in the case of a glucose sensor, which in turn creates more current, or signal, from the sensor. In this way, the bilateral biosensor is able to operate linearly over a wide range of analyte concentration without sacrificing sensitivity.

In one embodiment, the back side of the pore is covered with a back membrane. One function of the back membrane is to permit preferential supply of a co-substrate or reagent from the back of the sensor. Additionally, if there is a fluid pressure differential across the pore, the back layer prevents fluids from freely flowing through the pore. Fluid flow is to be distinguished from diffusion. Diffusion is required for pore function whereas fluid flow interferes with it. The back membrane layer is selected to be permeable to the co-substrate or co-reactant. In the case of a glucose sensor, the layer is oxygen permeable. Any of a variety of oxygen permeable films can be used for this purpose. Useful materials are silicone rubbers and PTFE. A more specific example is Dow Corning 3140 (a silicone rubber reaction product of hydroxy terminated dimethylsiloxane, trimethylated silica and methyltrimethoxysilane). Another example of a material that can be used is Sylgard 184 (a silicone rubber reaction product of dimethylvinyl dimethylsiloxane, dimethylvinylated and trimethylated silica, and tetra (trimethylsiloxy) silane). Silicone based hydrogels, such as PDMS, silicone hydrogels based on urethane block siloxanes, fluorinated side chain siloxanes, and siloxane macromers, should also be useful, as well as 4-methyl-1-pentane polymer.

In another embodiment the sensor is constructed without the back membrane. In this embodiment, the enzyme membrane and/or the barrier membrane may provide the desired permeability characteristic to deliver the co-substrate or other reagent to the site of the reaction with the analyte. In particular, a back membrane may not be required if a buffer is delivered from the back of the sensor.

In FIG. 1 is shown one manifestation of a bilateral sensor in accordance with this invention. The drawing depicts a glucose sensor based upon immobilized glucose oxidase. It represents the porous sensor 10 in its most basic form, as a single pore 12 through a thin film of Kapton™ 14. The walls of the pore 12 and one face of the film have been coated with platinum 16. A thin membrane 18 is formed across the face of the pore using poly(vinylalcohol) (PVA). The immobilized enzyme layer 20 is formed immediately behind the PVA, this is followed by a thin, oxygen-permeable layer of silicone 22.

Having, described the structure of bilateral pore sensors in accordance with various embodiments of the invention, the process for making the sensor will be described. The porous support, e.g., laser perforated polyimide, can be obtained commercially prepared by one of the processes that has already been described. An electrode is deposited on the porous substrate such that a metal layer is formed on the inside walls and/or immediately adjacent the back face of the pore. To form the electrode, in one embodiment the surface is coated with a 3000 Angstrom film of a diamond-like carbon amorphous film via chemical vapor deposition (CVD) and then DC sputtered with 200 anstroms of chromium or titanium followed by 2000 angstroms of platinum in a high vacuum. In another embodiment, the electrode can be formed by simply sputter depositing platinum on the wall of the pore.

A polymeric film is formed at the face of the pore by filling the pore from the back with the PVA solution (e.g., a 5 wt % solution of 100% hydrolyzed PVA, molecular weight=86,000) and removing the excess, allowing approximately one pore volume of solution to remain in the pore to evaporate. During evaporation the solution is drawn to the narrow end of the pore due to the larger capillary forces which exist at the smaller diameter end. This action creates a film at the small end of the pore. After drying at 50° C. for thirty minutes this film can be thermally cured to cross-link the PVA making it less apt to re-dissolve when exposed to potential solvents. This can be accomplished by exposure to temperatures of about 135° C. to 170° C. for a period of two hours.

After forming the outer membrane, the enzyme-containing layer may be formed by filling the pore with a solution containing water, buffer salts, the enzyme of interest and other cross-linking agents, e.g. glutaraldehyde, which serve to immobilize the enzyme and entrap it within the layer. The enzyme solution used in one embodiment is made up of glucose oxidase (12.5 mg) in a solution (125 μl) of buffer salts (citrate-succinate buffer, pH 5.5). Glutaraldehyde (187.5 μl of 2.5% solution) is added to this mixture to induce chemical cross-linking of the oxidase protein. In applying the enzyme layer after the PVA membrane is in position, it is important to avoid "bubbles." That is the enzyme membrane solution should be applied so that it flows down the sides of the pore. If the enzyme membrane solution covers the pore, air in the pore may become trapped and prevent the enzyme from filling the pore and cause the enzyme membrane to form as a bubble or dome over the back of the pore. By adjusting the composition and concentration of the enzyme membrane and applying it so that it flows down the walls of the pore, formation of bubbles or unfilled pores is avoided. Many other methods of enzyme immobilization may work in this way and are generally known to those skilled in the art. In one embodiment after drying at room temperature for thirty minutes the enzyme layer e.g., may be covered by a thin layer, 1 to 20 microns, of liquid silicone rubber, which is then cured (e.g., 24 hours) before the sensor is ready for use.

Figure 2:
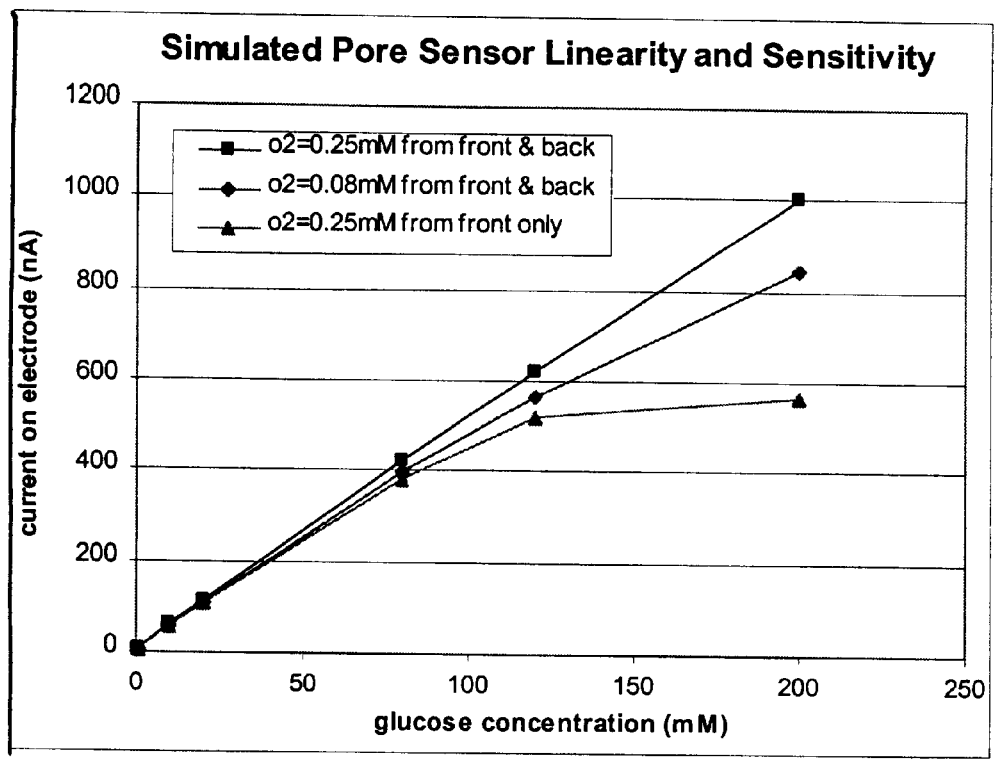
FIG. 2 is a graph of electrode current versus glucose concentration based upon a computer simulation of a sensor having a micro porous architecture for different oxygen concentrations ($O_2$) at the front and back faces of the sensor.
Figure 3:
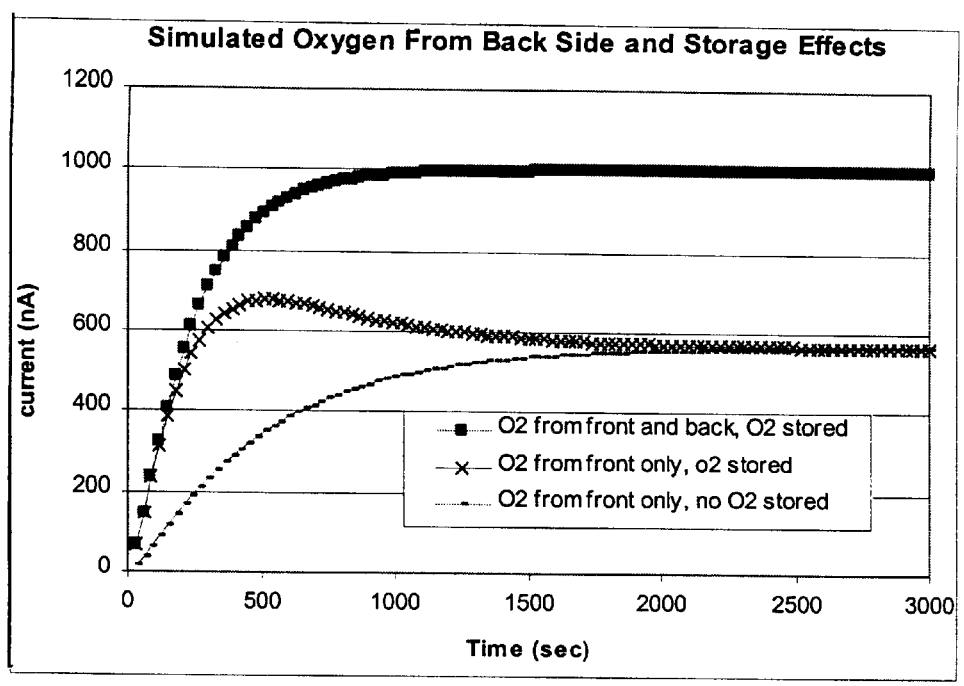
FIG. 3 is a graph of electrode current versus time based upon a computer simulation of a sensor in accordance with one embodiment of the invention.

FIGS. 2 and 3 are graphs based upon a computer simulation. As shown in FIG. 2, at oxygen concentrations of 0.25 mM with oxygen only supplied from the front of the sensor, the sensor exhibits a linear response only up to about 80 mM (see the triangle line). With additional oxygen supplied from the back (but maintaining a total oxygen concentration of 0.25 mM), the sensor's linearity extends up to 200 mM (see the square line). Even at lower oxygen levels (0.08 mM), with oxygen supplied from both sides, the linearity and sensitivity of the sensor are higher than that without oxygen supplied from the back (see the diamond line).

As shown in FIG. 3, with oxygen supplied from the back, the sensor's sensitivity is almost double, and the time to reach equilibrium is much less (see the square line and blue cross line). With oxygen initially stored inside the pore, the sensor's response is much faster and it displays much higher sensitivity during the initial stage (see the cross line) compared to the case without oxygen storage (the dash line).

Experimental data has also been collected for this sensor with bilateral influences. Conditions were set up such that oxygen and glucose concentrations could be controlled in front of, and behind the sensor. Sensors, similar to the one depicted in FIG. 1 of this document were constructed on Kapton™ film using laser poration techniques and thin film metalization.

A series of experiments were performed in which the backsides of the sensors were exposed to gases containing different amounts of oxygen and the front sides of the sensors were exposed to various glucose concentrations. Performance characteristics (e.g. linearity and sensitivity) were measured after equilibrium was established for each condition.

In one such experiment, from time 0 to 24 h, the backside of the sensors was exposed to air (normal oxygen levels, ~21%). At t=26 h, the backside of the sensors was exposed to pure nitrogen ($N_2$) for 3 hours (26–29 h), then the nitrogen was removed and the array was allowed to equilibrate with atmospheric oxygen for one hour. Finally, the backside of the sensors was exposed to compressed air for one hour.

It was observed that the sensitivity of the sensors (as expressed by the average current response) clearly decreases (more than 50%) when the backside of the sensors was exposed to pure $N_2$: from 26–27 nA (normal oxygen) to about 12 nA (nitrogen). The linearity of the response was also significantly affected. Linearity, expressed as the ratio of the current response of the sensors when exposed to 40 mM versus 20 mM glucose, decayed from 1.9–2.0 (normal oxygen) to 1.3 (nitrogen). These experiments prove that removing the oxygen supply from the back of the sensor affects the supply of oxygen to the enzyme layer inside the pore. The signal recovers when the sensors are provided again with oxygen from the backside. The effect is real and is not due to the flow of nitrogen gas (pressure effect) as evidenced by the response of the sensors when the sensors are exposed to compressed air (same flow rate of the previous nitrogen purge).

Having described the invention in detail and by reference to specific embodiments thereof, it will be recognized that numerous modifications and variations are possible without departing from the spirit and scope of the invention as defined by the following claims.

What is claimed:

1. A microporous sensor for detecting an analyte comprising a substrate having a front face and a back face, and at least one pore extending through the substrate that interacts with the analyte, a membrane containing an enzyme disposed near the front face of the pore, an electrode, and a back membrane disposed at the back face of the pore, the back membrane being permeable to a co-substrate or other reagent.

2. The sensor of claim 1 wherein the back membrane is able to supply sufficient co-substrate or other reagent to the pore to improve sensor performance.

3. The sensor of claim 1 wherein the enzyme is selected from the group consisting of glucose oxidases, galactose oxidases and uricases.

4. The sensor of claim 3 wherein the enzyme is useful in a glucose oxidase.

5. The sensor of claim 3 wherein the sensor additionally includes a barrier film interposed between the enzyme-containing membrane and the analyte.

6. The sensor of claim 5 wherein at least one pore is about 0.02 to 200 microns in diameter.

7. The sensor of claim 6 wherein the substrate is about 1 to 1,000 microns thick.

8. The sensor of claim 7 wherein the substrate is a film of a polymer selected from the group consisting of polyimide, polycarbonate and polyethylene terephthalate.

9. The sensor of claim 6 wherein the back membrane is polytetrafluroethylene or silicone rubber.

10. The sensor of claim 9 wherein the back membrane is silicone rubber.

11. The sensor of claim 10 wherein the barrier film is polyvinyl alcohol.

12. The sensor of claim 11 wherein the pores are in a random or ordered pattern.

13. The sensor of claim 12 wherein the pores are laser drilled.

14. The sensor of claim 6 wherein the substrate is a cyclotron irradiated film.

15. The sensor of claim 1 wherein the sensor includes a plurality of pores.

16. The sensor of claim 1 wherein the back membrane is permeable to a cosubstrate.

17. The sensor of claim 16 wherein the back membrane is permeable to oxygen.

18. The sensor of claim 1 wherein the electrode is formed on the wall of the pore.

19. The sensor of claim 1 wherein the electrode is formed at the perimeter of the pore on the back face of the substrate.

20. A glucose sensor comprising a substrate having a front face and a back face and at least one pore extending through the substrate, a membrane containing an enzyme that reacts with glucose disposed near the front face of the pore, an electrode in electrochemical contact with the enzyme-containing membrane, and a back membrane that is permeable to oxygen such that oxygen can be supplied from the back face of the pore to the enzyme-containing membrane for reaction with glucose thereby providing the oxygen to the enzyme in quantities that improve sensor performance.

21. The sensor of claim 20 wherein the enzyme is selected from the group consisting of glucose oxidases, galactose oxidases and uricases.

22. The sensor of claim 21 wherein the sensor includes a plurality of pores.

23. The sensor of claim 22 wherein the electrode is formed on the wall of the pore.

24. The sensor of claim 22 wherein the electrode is formed at the perimeter of the pore on the back face of the substrate.

25. The sensor of claim 20 wherein a barrier film of polyvinyl alcohol is provided over the enzyme-containing membrane on the front face of the pore.

26. The sensor of claim 25 wherein the pores are about 0.02 to 200 microns in diameter.

27. The sensor of claim 26 wherein the substrate is about 1 to 1,000 microns thick.

28. A method for detecting an analyte which comprises:

providing a microporous sensor including a substrate having a front face and a back face and at least one pore extending through the substrate, a membrane containing an enzyme disposed near the front face of the pore, an electrode and a back membrane disposed at the back face of the pore;

contacting a fluid suspected of containing an analyte with the front face of the substrate in the presence of a co-reactant for detecting the analyte; and supplying said co-reactant from the back face of the substrate through the back membrane and the pore.

* * * * *